US009545293B2

(12) United States Patent
Sollberger et al.

(10) Patent No.: US 9,545,293 B2
(45) Date of Patent: Jan. 17, 2017

(54) DENTAL IMPLANT, ABUTMENT FOR A DENTAL IMPLANT AND COMBINATION THEREOF AND AN IMPLANT SET

(75) Inventors: David Sollberger, Binningen (CH); Christoph Solér, Zwingen (CH); Alex Schär, Riehen (CH)

(73) Assignee: CAMLOG BIOTECHNOLOGIES AG, Basel (CH)

( * ) Notice: Subject to any disclaimer, the term of this patent is extended or adjusted under 35 U.S.C. 154(b) by 0 days.

(21) Appl. No.: 13/574,383

(22) PCT Filed: Jan. 13, 2011

(86) PCT No.: PCT/EP2011/050407
§ 371 (c)(1),
(2), (4) Date: Jul. 20, 2012

(87) PCT Pub. No.: WO2011/089057
PCT Pub. Date: Jul. 28, 2011

(65) Prior Publication Data
US 2012/0301850 A1 Nov. 29, 2012

(30) Foreign Application Priority Data
Jan. 21, 2010 (EP) .................................... 10151292

(51) Int. Cl.
*A61C 8/00* (2006.01)

(52) U.S. Cl.
CPC .............. *A61C 8/005* (2013.01); *A61C 8/008* (2013.01); *A61C 8/0066* (2013.01); *A61C 8/0069* (2013.01); *A61C 8/0068* (2013.01)

(58) Field of Classification Search
CPC ...... A61C 8/0022; A61C 8/0048; A61C 8/005; A61C 8/0066; A61C 8/0069; A61C 8/008; A61C 8/0068
USPC ....................................... 433/172–176, 201.1
See application file for complete search history.

(56) References Cited

U.S. PATENT DOCUMENTS

| | | | | | |
|---|---|---|---|---|---|
| 4,960,381 | A | * | 10/1990 | Niznick | A61C 8/0039 433/173 |
| 5,076,788 | A | * | 12/1991 | Niznick | A61C 8/0018 433/173 |
| 5,195,892 | A | * | 3/1993 | Gersberg | A61C 8/0022 433/173 |

(Continued)

FOREIGN PATENT DOCUMENTS

| | | |
|---|---|---|
| AT | 400804 | 3/1996 |
| CA | 2672363 | 6/2008 |

(Continued)

*Primary Examiner* — Cris L Rodriguez
*Assistant Examiner* — Hao D Mai
(74) *Attorney, Agent, or Firm* — Davis & Bujold PLLC; Michael J. Bujold (57) ABSTRACT

The invention relates to an implant (10) serving to receive an abutment (110). The implant (10) has a receiving opening (15) in which a connection region (115) of the abutment (110) can be inserted. The receiving opening (15) and the connection region (115) have a conical section (17) or (117) and an indexing section (18) or (118). The total conical angle equals 6 to 20° and the indexing length f of the implant (10) or the indexing length F of the abutment (110) equals at least 90% of the conical section length k of the implant (10) or of the conical section length K of the abutment (110), typically more than 1.6 mm.

20 Claims, 7 Drawing Sheets

(56) References Cited

U.S. PATENT DOCUMENTS

| | | | |
|---|---|---|---|
| 5,588,838 A | 12/1996 | Hansson et al. | |
| 5,782,918 A * | 7/1998 | Klardie | A61C 8/005 433/172 |
| 5,823,776 A * | 10/1998 | Duerr | A61C 8/005 433/173 |
| 6,116,904 A * | 9/2000 | Kirsch | A61C 8/0018 433/173 |
| 6,626,911 B1 * | 9/2003 | Engman | A61C 8/0022 433/172 |
| 7,309,231 B2 * | 12/2007 | Engman | 433/173 |
| 8,123,524 B2 * | 2/2012 | Anitua Aldecoa | A61C 8/005 433/173 |
| 8,794,966 B2 * | 8/2014 | Hung | A61C 8/0089 433/173 |
| 8,920,170 B2 * | 12/2014 | Krivoruk | 433/172 |
| 2002/0177105 A1 * | 11/2002 | Engman | A61C 8/005 433/173 |
| 2003/0113690 A1 * | 6/2003 | Hollander | A61C 8/005 433/173 |
| 2004/0101808 A1 * | 5/2004 | Porter et al. | 433/173 |
| 2005/0287497 A1 * | 12/2005 | Carter | 433/173 |
| 2007/0099153 A1 * | 5/2007 | Fromovich | A61C 8/0022 433/174 |
| 2008/0131840 A1 | 6/2008 | Chen | |
| 2008/0261175 A1 * | 10/2008 | Hurson | A61C 8/0025 433/173 |
| 2008/0261176 A1 * | 10/2008 | Hurson | 433/174 |
| 2014/0120498 A1 * | 5/2014 | Grosse | A61C 8/0054 433/174 |

FOREIGN PATENT DOCUMENTS

| | | |
|---|---|---|
| DE | 10231743 | 2/2004 |
| DE | 10315399 | 9/2004 |
| DE | 102005001792 | 7/2006 |
| EP | 1203567 | 5/2002 |
| EP | 1396236 | 3/2004 |
| EP | 1728486 | 12/2006 |
| JP | 2000-501012 | 2/2000 |
| JP | 2008-504883 | 2/2008 |
| WO | 96/29020 | 9/1996 |
| WO | 97/20518 | 6/1997 |
| WO | 0027300 A1 | 5/2000 |
| WO | 03/020154 | 3/2003 |
| WO | 2007/134686 | 11/2007 |

* cited by examiner

DENTAL IMPLANT, ABUTMENT FOR A DENTAL IMPLANT AND COMBINATION THEREOF AND AN IMPLANT SET

The invention relates to a dental implant, an abutment for a dental implant, a combination of such an implant and abutment, and an implantation set, having the features of the preamble of the independent claims.

Dental implants and associated abutments are known in many different designs. The dental implant is typically formed by a substantially cylindrical body. At its coronal end, the body has a receiving opening into which a so-called abutment can be inserted. Here, and in the text below, coronal designates the direction toward the crown or the tooth that is to be fitted. In this context, cervical designates the direction toward the tooth root.

The abutment insertable into the receiving opening is used, in a manner known per se, to receive a tooth replacement either directly or indirectly. It is already known for the receiving opening in the implant and for a corresponding mating surface to be given a conical shape. This is done in an effort to achieve the best possible mechanical connection and seal between abutment and implant, so as to avoid forming a gap in which liquids or bacteria can settle. However, conical arrangements of this kind are associated with various disadvantages. For example, when the impression is subsequently taken, a height shift arises on account of tolerances in the angle and diameter of the cone. At the same time, because of the cone, the external diameter of the abutment in the lower area is smaller than in comparable abutments with non-conical sections. In this area, there is typically an indexing area for rotation securing or rotation positioning between abutment and implant. Such indexing areas typically produce, in the circumferential direction, a form fit with a non-round contour, e.g. by a polygon or by grooves and cams. Because of the thinner wall thickness, the possibilities as regards the design of the indexing area are reduced. In particular, problems concerning strength may also arise. This can cause difficulties especially if the indexing area in the implant also serves for contact with a screwing-in tool used to screw in the implant.

Abutments and implants with corresponding conical sections are known, for example, from AT 400 804 B, EP 1 396 236 A1, EP 1 203 567, DE 102 31 743 A1, EP 1 728 486 A1 or DE 10 2005 001 792 A1. However, all of these solutions are associated with the disadvantages mentioned above and with others too.

It is therefore an object of the present invention to avoid the disadvantages of the known solutions, in particular to make available a dental implant and an abutment and also an implantation set, which ensure a reliable and firm connection between implant and abutment, which as far as possible prevent bacteria from settling in a gap between implant and abutment, and which permit a good transfer of force between a screwing-in tool and the implant during screwing-in of the implant and also permit a reliable impression of the implant situation in the mouth.

According to the invention, these and other objects are achieved by a dental implant, an abutment and an implantation set according to the features of the characterizing part of the independent claims.

The dental implant according to the invention serves in a manner known per se for insertion into a jaw bone. The implant has, at the coronal end, a receiving opening for an abutment. The receiving opening, seen from the coronal end, has a cone section with a defined cone length and an indexing section with a defined indexing length. According to the invention, the cone section has a total cone angle in the range of 6° to 20°, preferably 10° to 18°, particularly preferably 15°. In interaction with a correspondingly shaped cone on the abutment, a self-locking connection is obtained when the abutment is inserted into the implant. An additional stability of the connection is thereby achieved. Moreover, the indexing length is at least 90% or, depending on the implant diameter, preferably about 95% to 125% of the cone length. In this way, despite the external diameter of the abutment being reduced because of the cone, there is sufficient stability in the connection between abutment and implant. Moreover, a sufficiently large engagement surface is made available for a screwing-in tool. The indexing section serves for rotation positioning and rotation securing between abutment and implant and at the same time also as an engagement surface for a screwing-in tool. Seen in the axial direction, the indexing section is preferably at least 1.6 mm in length. In principle, it is conceivable to design the indexing section in a manner known per se with a polygon or other non-round contours. However, an indexing section is preferred which, as described below, is designed with a groove/cam connection.

According to a preferred embodiment of the invention, the indexing section has a surface in which at least one radially outwardly extending groove with a defined groove length is arranged. The groove can be brought into engagement with a cam of an abutment. Typically, the surface is at least partially cylindrical. At the same time, it is dimensioned and toleranced in such a way that it forms a guide surface for a correctly inserted abutment.

It is also preferable that the groove length extends substantially over the entire length of the indexing section, in particular over at least 70%. In this way, it is possible to maximize the contact between the engagement surface of the groove and a corresponding engagement surface on a cam of a screwing-in tool or of an abutment, such that screwing-in forces or moments can be transferred without plastic deformation and such that the force introduced per surface unit can be minimized. This deformation would have an influence on the accuracy of the impression and positioning of the abutment. The bottom of the groove, directed toward the lower end of the implant, is preferably beveled. The angle of the bevel corresponds particularly preferably to the angle of a corresponding chamfer on a cam of an abutment.

In the cervical direction, the indexing section of the implant is preferably adjoined directly by a thread section for receiving an abutment screw. In other words, this means that the form-fit end in the implant is not adjoined by any further area serving to receive or guide the abutment.

Particularly preferably, the surface of the indexing section has an external diameter which is greater than 80% of the external diameter of the groove. In this way, the external diameter of a corresponding indexing section of an abutment can be made as large as possible. At the same time, however, the external diameter of the indexing section should not be too close to the external diameter of the groove, such that a sufficiently large groove depth is still ensured.

It is also preferable that the groove has a radially extending groove surface (or a radially extending groove surface on both sides), which is greater than 0.22 mm$^2$.

At the same time, the groove length is preferably greater than 500% of the groove depth. The groove depth is understood as the distance between the surface of the indexing section and the external diameter of the groove.

According to another preferred embodiment, the small cone diameter (i.e. the diameter at the cervical end of the cone section) is greater than or the same as the external diameter of the groove. In this way, a platform is formed which defines an intermediate position during the insertion of the abutment.

It is also preferable that a circumferential platform surface is formed between the cone section and the indexing section of the implant. The groove in this case extends in the axial direction as far as this platform surface. Such a platform surface makes it possible to define an intermediate position. An abutment can be inserted into the implant until the undersides of the corresponding cams of the abutment bear on the platform surface. By turning the abutment to a position in which the cams on the abutment are aligned with the grooves in the implant, the abutment can then be brought to the desired end position. The insertion procedure comprising the steps of "inserting axially", "turning in the circumferential direction" and "moving axially to the end position" is particularly intuitive for the user. Insertion in an undesired intermediate position is thus prevented.

A further aspect of the invention concerns an abutment for a dental implant, in particular for the implant described above. The abutment has a surface for directly or indirectly receiving a tooth replacement. The abutment also has a connection area for connection to the implant. The connection area can typically be inserted into the aforementioned receiving opening of the implant. The abutment can be fixed in the implant by means of an abutment screw in a manner known per se. The connection area of the abutment has a cone section with a defined cone length. In the cervical direction, the connection area is adjoined by an indexing area with a defined indexing length. The cone section of the abutment has a total cone angle of 6° to 20°, preferably 10° to 18°, and particularly preferably 15°. The indexing length of the abutment is at least 90%, preferably 95% to 125% of the cone length of the abutment. In interaction with the abutments as described above, particularly stable connections are thus obtained. The indexing length is preferably at least 1.6 mm. Toward the cervical end, the indexing section is delimited by the end of the form-fit elements. Toward the coronal end, the indexing section is delimited by the end of a substantially cylindrical section on or in which the form-fit elements are mounted.

The abutment preferably has, in the indexing section, a surface from which at least one cam extends radially outward. The cam can be brought into engagement with the corresponding grooves of an implant. Particularly preferably, this surface of the abutment is at least partially cylindrical. It is also dimensioned and toleranced in such a way that it forms a guide surface for a surface of the indexing section of an implant when the abutment is correctly inserted into the implant. The abutment can thus be made shorter than, for example, the abutment disclosed in EP 1 728 486, since it is possible to do without a further cervical guide section. Moreover, the guide section can be designed with a relatively large diameter, which lessens the sensitivity to manufacturing tolerances. Finally, a guide section designed in this way ensures that, during insertion, the abutment is guided at a very early stage in the implant.

Typically, in the case of a diameter of ca. 2 to 3 mm, the corresponding guide surface on the abutment and the guide surface on the implant are produced with such a tolerance that the maximum play between the surfaces is less than 0.06 mm.

The cams preferably extend over substantially the entire area of the indexing section. Substantially the entire indexing area is understood as a length of at least 70%. In this way, the contact surface between the grooves and the cams is maximized, resulting in a better force distribution and a more stable connection. However, the cams on the abutment can also be slightly longer, typically at least 75% of the indexing area. At its upper end, i.e. toward the cone section, the cylindrical surface between the cams can have an end surface which is beveled with respect to a plane perpendicular to the axis. The bevel is preferably 40° to 50°, in particular approximately 45°. It is also preferable that, in the direction of the cone section, this end surface is adjoined by a circumferential cylindrical surface. The external diameter of this cylindrical surface corresponds in particular to the external diameter of the cam on the abutment, such that a surface with constant cylinder radius is obtained about the circumference.

According to another preferred embodiment, the abutment has, adjacent in the cervical direction to the indexing section at the cervical end, a front surface with an opening. A thread section of an abutment screw can be guided through this opening. In other words, this means that the indexing section forms the last element of the abutment in the cervical direction (with the exception of the abutment screw, which is not formed in one piece with the abutment body). In particular, in the cervical direction, the indexing section is not followed by any further guide sections or guide elements.

It is also preferable that the external diameter of the surface of the indexing section of the abutment is greater than 80% of the external diameter of the cam. This ensures that the surface of the indexing section, which surface at the same time forms a guide surface as described above, can be made as large as possible. In addition, at larger dimensions, identical manufacturing tolerances have less influence on play.

It is also preferable that the cam has a radially extending cam surface which is greater than 0.22 mm$^2$. The cam length is preferably at least 500% greater than the cam depth. Cam depth is understood as the distance between the external diameter of the cam and the surface of the indexing section of the abutment. By designing the cams with a sufficient length, it is possible, despite the small cam depths, for the cam surface, which forms a contact surface for grooves of the implant, to be made sufficiently large to transfer the screwing-in moment during insertion of the implants.

It is also preferable that the diameter of the cone, at the cervical end thereof, is greater than or the same size as the diameter of the cams.

Moreover, at its cervical end, the cam preferably has a chamfer. The insertion of the cams into the grooves of the implant is made easier by such a chamfer. The chamfer forms an insertion aid.

The abutment also preferably has an emergence profile with a defined configuration: The cone section of the abutment, which section emerges from the implant, is adjoined by a short cylindrical section and then, seen in a sectional plane through the axis of the abutment, by a concave area and, thereafter, a convex area, which simulates the natural tooth shape.

It is also preferable that the surface of the indexing section of the abutment is not completely cylindrical. Undercuts are preferably present between the cam surfaces of the cam and the surface serving as guide surface. Such undercuts permit particularly precise production of the indexing section and of the guide surface on the abutment.

The abutment, provided with an axial bore, can be provided with an additional thread in the area of the bore. The thread serves to receive a disassembly tool. Since the cone angle is chosen such that, with the abutment inserted, self-locking is obtained between the cone surfaces of the abutment and of the implant, it can sometimes happen that the abutment cannot easily be removed. By virtue of this thread, the abutment can be uncoupled by a disassembly tool being secured in the abutment.

According to a further aspect, the invention relates to a combination of an implant as described above and of an abutment as described above. The indexing sections of implant and abutment and the cone sections of implant and abutment are dimensioned and shaped in such a way that, when the abutment is inserted into the implant, the cone sections at least partially touch each other and the indexing sections are in engagement with each other. The surfaces via which the cone sections touch each other are thus maximized as far as possible within the scope of the tolerances.

Particularly preferably, the cone sections on abutment and implant are toleranced in such a way that, in any conceivable pairing between implant and the associated abutment, contact between the cone sections takes place at the coronal edge of the cone section of the implant within the scope of the tolerances. Although a gap between abutment and implant can never really be ruled out on account of tolerances in the cone angle, the gap in any case will not then form at the coronal end but instead inwardly offset therefrom. This avoids liquids collecting in a corresponding gap.

Moreover, the contact between the cone sections in the area of the coronal edge provides particularly stable fastening of the abutment in the implant. There is as it were a two-point support, on the one hand at the upper coronal edge and on the other hand in the area of the guide surfaces between the grooves and the cams.

It is also preferable that the surfaces of the indexing sections between the cams of the abutment and between the grooves of the implant are dimensioned such that the abutment is guided in the implant through contact between the surfaces of the indexing sections. The surfaces are typically dimensioned as follows such that, in the case of guide surfaces with a diameter of 2 to 3 mm, typically 2.1 mm, the maximum play between the guide surfaces is 0.06 mm.

According to yet another preferred embodiment, the abutment has an abutment screw in which the length, in particular the arrangement, of the thread is dimensioned such that the abutment screw cannot be brought into engagement with a thread section in the implant as long as the abutment bears with an end face of its cams at the cervical end on the platform of the implant. This avoids a situation where the abutment is inadvertently secured in the implant, by tightening of an abutment screw, before the abutment has reached the correct position.

According to a further aspect, the invention relates to an implantation set. The implantation set has at least one implant and at least one abutment. At its coronal end, the implant is designed with a receiving opening for the abutment. The receiving opening has an implant cone section adjacent to the coronal end. The implant and the abutment are preferably designed as described above. The abutment can be inserted into the receiving opening of the implant and has an abutment cone section that can be brought into engagement with the implant cone section.

The implantation set also has at least one auxiliary element. For various tasks in the context of implantation, auxiliary elements are used, typically occlusion screws, gingiva formers, provisional abutments or impression elements. Such elements are known per se to a person skilled in the art. According to the invention, the auxiliary element is designed in such a way that, when it is inserted into the implant, it does not touch the implant cone surface and bears with a contact surface on a front edge of the implant. This design of the auxiliary elements affords various advantages. First, the cone surface of the implant remains substantially unaffected by the auxiliary elements. Damage to the cone surface by the auxiliary elements is therefore substantially excluded. Second, the auxiliary parts can be more easily uncoupled, because there is no self-locking between the cone surfaces. At the same time, vertical shifts are reliably avoided when taking an impression, since it is not the cone surface but instead the front face of the implant that defines the vertical position of the impression element.

Particularly preferably, the auxiliary element has, in the area of the contact surface, an external diameter greater than the external diameter of the abutment in this area. In this way, especially in the case of a gingiva former, an occlusion screw or a provisional abutment, the bone or the gum can be shaped to the extent that the insertion of the final abutment is not impaired.

Moreover, in the case of an auxiliary element designed as gingiva former, the external diameter in the area of the contact surface is greater than the corresponding external diameter of an auxiliary element designed as impression element. This avoids the gum interfering with the impression-taking.

The invention is explained in more detail below on the basis of illustrative embodiments and with reference to the drawings, in which.

Figure 1:
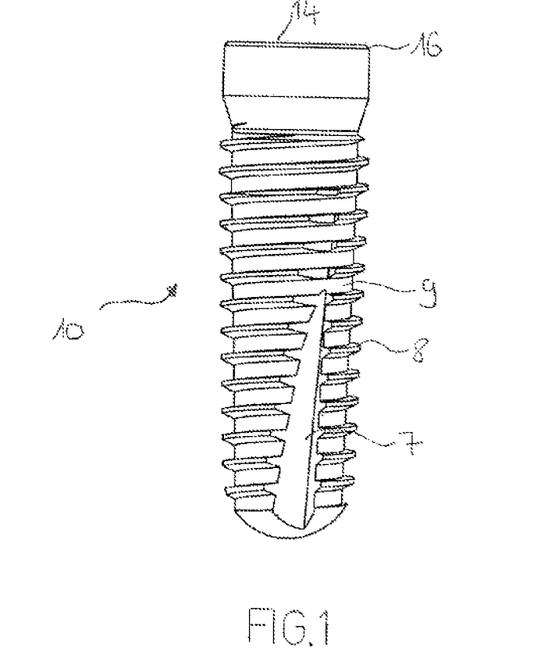
FIG. 1 shows a side view of an implant according to the invention.

FIG. 1 shows an implant 10. The implant 10 has a main body 9 with a thread 8 and a cutting edge 7 in a manner known per se. The implant 10 is inserted with the main body 9 into a jaw of a patient, such that, depending on the situation, a coronal end 16 of the implant 10 with an end face 14 protrudes slightly from the bone or lies slightly lower.

Figure 2:
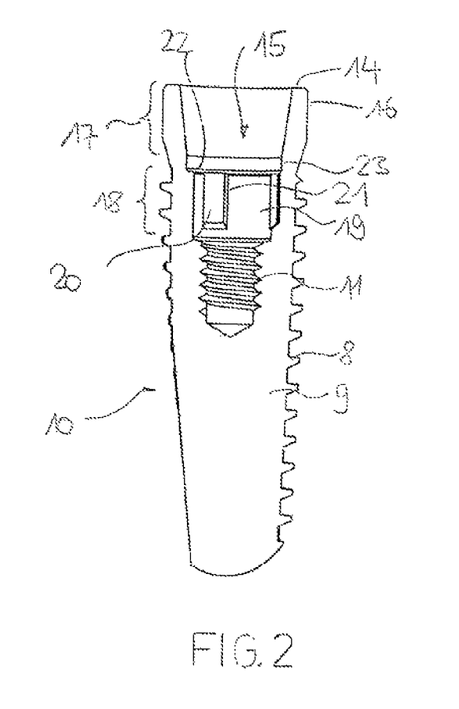
FIG. 2 shows a cross section through the implant according to FIG. 1, along a central longitudinal axis.

FIG. 2 shows a cross section through a central axis of the implant according to FIG. 1. Adjacent to the coronal end 16, the implant 10 has a receiving opening 15 for receiving an abutment (see FIG. 4a). Directly adjacent to the coronal end 16, the receiving opening 15 has a cone section 17. The cone section 17 is adjoined directly by a short cylindrical section 23. The cylindrical section 23 is adjoined by an indexing section 18. The indexing section 18 is formed by a substantially cylindrical surface 19, in which are arranged three grooves 20, uniformly distributed about the circumference. The grooves 20 extend radially outward from the surface 19. The grooves have lateral groove surfaces 21, which can come into engagement with corresponding cam surfaces of an abutment (see FIG. 4a) or of a screwing-in instrument or of other auxiliary elements and thus form a rotation securing means and allow transfer of the screwing-in torques.

A platform 22 is formed between the cylindrical section 23 and the indexing section 18. The abutment (see FIG. 4a) rests with the cervical underside of its cams on this platform surface 22 when the cams of the abutment are not exactly flush with the grooves 20 of the implant 10. An intermediate position is thereby defined. By turning the abutment relative to the implant 10, the cams and the grooves 20 can be oriented such that the abutment can be moved axially into an end position. The implant 10 also has a thread section 11. The abutment can be secured in the implant 10 by means of an abutment screw (see also FIG. 7). The abutment screw is designed with respect to the thread section 11 of the implant 10 in such a way that the abutment screw does not come into engagement with the thread section 11 when the abutment rests on the platform surface 22 in the intermediate position.

Figure 3A:
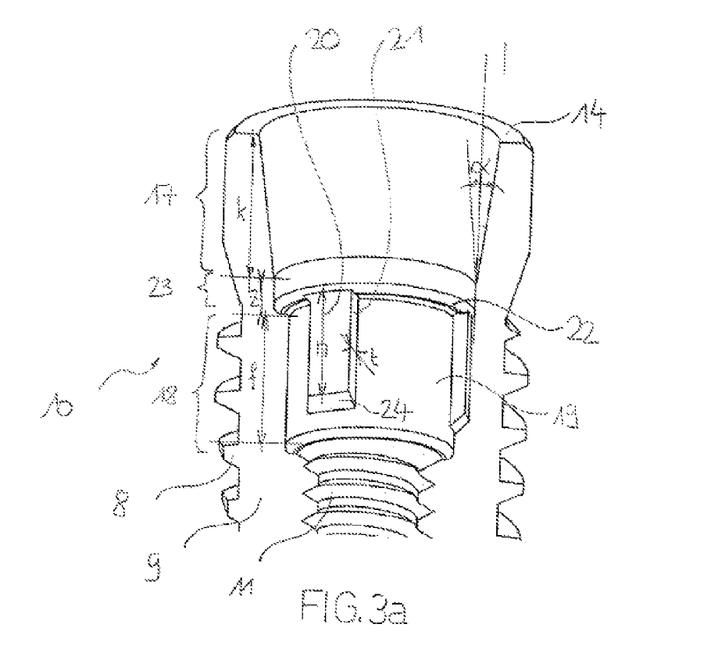
FIGS. 3a and 3b show enlarged views of the implant from FIG. 1 in the area of a receiving opening, in cross section.
Figure 3B:
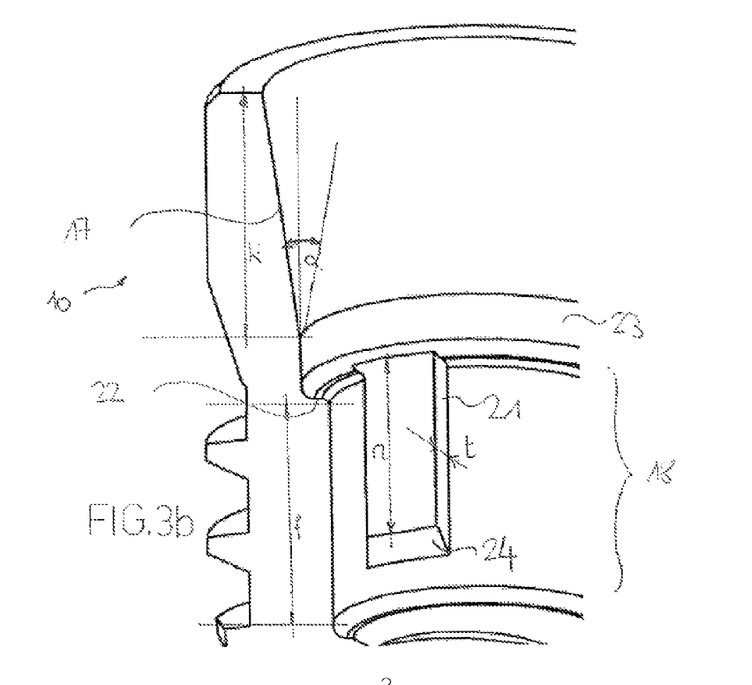

FIGS. 3a and 3b show enlarged cross-sectional views of the implant 10 in the area of the cone section 17 and of the indexing section 18. The same reference signs designate the same parts as in FIGS. 1 and 2. The cone section 17 extends at a total cone angle α of approximately 15°.

Typical dimensions of an implant and of an associated abutment are given below for an implant diameter of 3.8 mm. The cone section 17 has a cone length k of 1.9 mm. The length z of the cylindrical section 23 is 0.4 mm.

Compared to the cone section 17, the indexing section 18 is made relatively long in the axial direction. The indexing length f is 1.8 mm.

The grooves 20 formed in the indexing section 18 have a groove depth t of at least 0.18 mm and, in the axial direction, a groove length n of at least 1.35 mm. The groove 20 therefore extends in the axial direction over at least 75% of the indexing length f. The indexing length f of 1.8 mm is almost as long as the cone length k. By virtue of this particular choice of relatively long grooves, the groove surface 21 is made relatively large even though the groove depth t is slight. Deformations of the groove surface 21, for example through contact with a screwing-in tool, are thereby avoided.

A bevel is provided at the bottom 24 of the groove 20 as shown in FIG. 3b. Because of the bevel at the bottom 24, the groove depth n is slightly less radially outward than at the radially inner edge of the groove. The bevel of the groove (see also FIG. 8) corresponds approximately to the bevel at the lower edge of the cam (chamfer 125) of the implant.

Figure 4A:
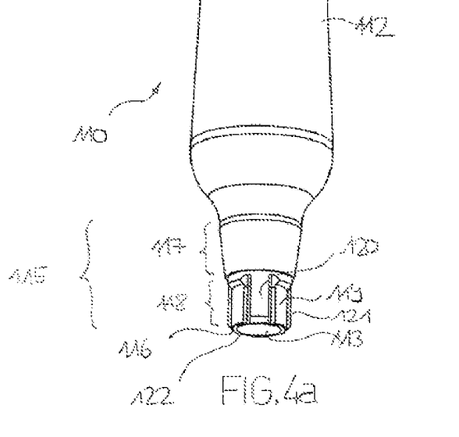
FIG. 4a shows a perspective view of an abutment according to the invention.

FIG. 4a shows a perspective view of an abutment 110 according to the invention. The abutment 110 has a surface 112, which serves to receive an artificial tooth directly or indirectly. For this purpose, it is also conceivable for the surface 112 to be worked, in particular ground. The abutment 110 has a connection area 115, with which it can be inserted into the receiving area 15 of the implant 10 (see FIG. 2). The connection area 115 has a cone section 117 which, toward the cervical end 116 of the abutment 110, is adjoined by an indexing section 118. The indexing section 118 is composed of a substantially cylindrical surface 119, from which three cams 120 distributed uniformly about the circumference extend radially outward. The cams 120 define lateral cam surfaces 121, which can be brought into engagement with the groove surfaces 21 of the implant (see FIGS. 3a and 3b).

Figure 5:
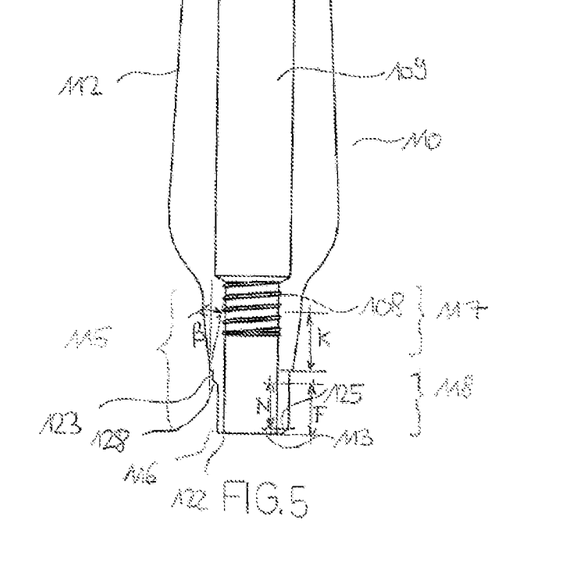
FIG. 5 shows a cross section through the abutment according to FIG. 4a along a central longitudinal axis.

At the cervical end 116, the abutment 110 has an opening 113 in its front face 122, which opening 113 forms the end of a continuous bore 109 (see FIG. 5). An abutment screw (see FIG. 7) can be guided through the opening 113.

Figure 4B:
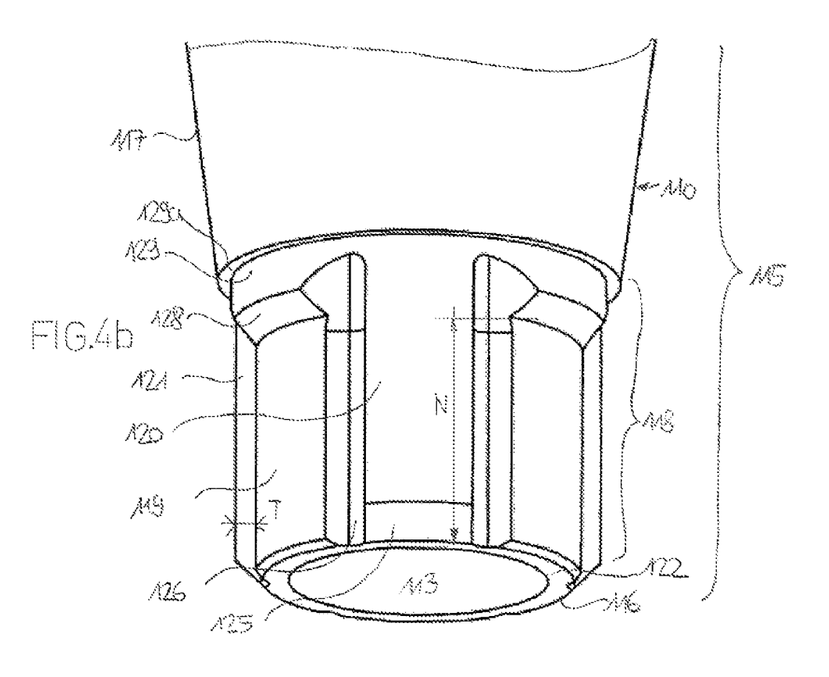
FIG. 4b shows an enlarged view of the abutment from FIG. 4a in a connection area.

FIG. 4b shows an enlarged view of the indexing section 118 of the abutment 110. In the axial direction, the cams 120 have a cam length N of 1.55 mm. Toward the cervical end 116 of the abutment 110, the cams 120 have a chamfer 125. Between the cams 120 and the surface 119, an undercut 126 is formed in the surface 119. The undercut 126 is mainly related to the production technology and permits particularly precise finishing of the surface 119, such that the latter can be finished sufficiently precisely to serve as a guide surface. The cams 120 have a cam depth T of 0.15 mm.

The cylindrical surface 119 between the cams 120 extends from the lower end of the abutment 110 over the indexing section 118, but not over the entire height thereof. Seen in the axial direction, the cylindrical section 119 is closed off toward the cone section 117 by an end face 128. The end face 128 is slightly beveled in relation to a perpendicular plane to the axis (see also FIG. 5). Further toward the cone section 117, the abutment 110 has a circumferential cylindrical surface 129. By way of a ring surface 129a extending perpendicularly with respect to the axis, the cylindrical section 129 merges into the cone section 117.

FIG. 5 shows a cross section through the abutment 110 from FIGS. 4a and 4b, along the central longitudinal axis. The abutment 110 has a bore 109 extending in the axial direction. The bore 109 is provided with an inner thread 108, which serves to receive a disassembly tool.

The cone section 117 has a total cone angle β of 15°. The cone section 117 has a cone length K of 1.9 mm. The indexing section 118 has an indexing length F of 1.95 mm. The cams have a cam length N of 1.55 mm, which corresponds substantially to the length of the indexing section 118. Arranged between the cone section 117 and the indexing section 118, there is a short cylindrical section 123, which is related to production technology and has no further function.

Figure 6:
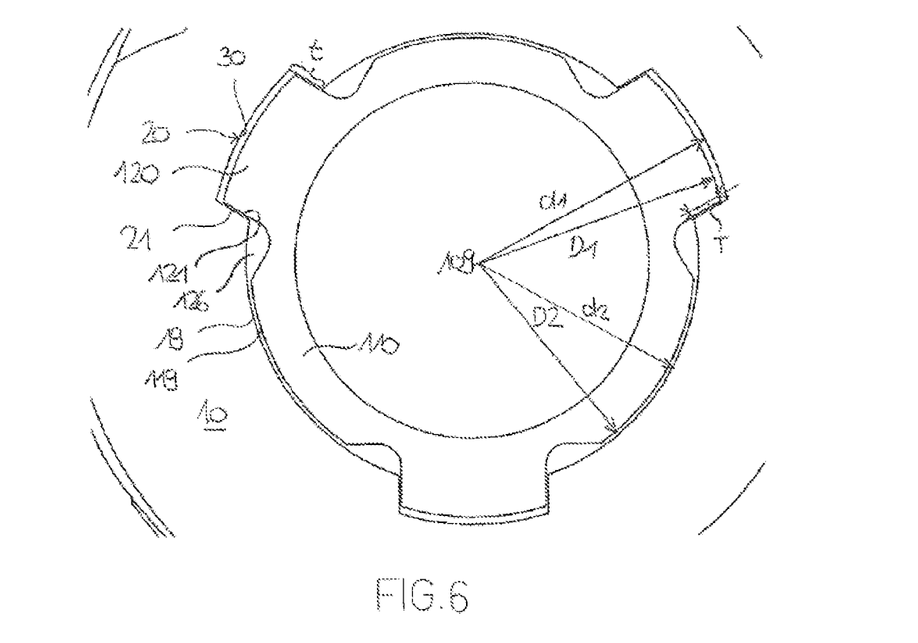
FIG. 6 shows a cross section through an implant according to the invention and an abutment according to the invention in an indexing area, along a plane perpendicular to the axis.

FIG. 6 shows a cross section through an abutment 110 inserted into an implant 10, along a plane perpendicular to the axis.

The cams 120 are in engagement with the grooves 20, such that the cam surfaces 121 contact the groove surfaces 21. The external diameter D2 of the surface 119 of the abutment 110 is substantially of the same dimension as the internal diameter d2 of the contact surface 19 of the implant 10. In this way, the surface 119 of the abutment between the cams 120 is guided on the surface 19 of the implant 10 between the grooves 20. The diameters D2 and d2 are both 2.1 mm and are toleranced such that the maximum play between the guide surfaces is not more than 0.06 mm. In addition, the minimum play is chosen such that the abutment can be guided into the receiving opening of the implant.

The external diameter D1 of the cams and the external diameter d1 of the grooves are likewise substantially the same. Here, however, a guide function is not essential, and therefore a gap 30 can exist. The diameters D1 and d1 are typically 2.4 mm and 2.45 mm, respectively. The cam depth T and the groove depth t result from the difference between the diameters D1 and D2 and the diameters d1 and d2, respectively. An undercut 126 is also formed between the surface 119 and the groove 120 of the abutment 110. The undercut 126 is not taken into account in defining the cam depth T.

If the external diameter of the surface 119 of the abutment and the internal diameter of the surface 19 of the implant 10 are each 2.1 mm, the cams 120 and the grooves 20, seen in the circumferential direction, have a cam width and groove width, respectively, of ca. 0.7 mm.

Figure 7:
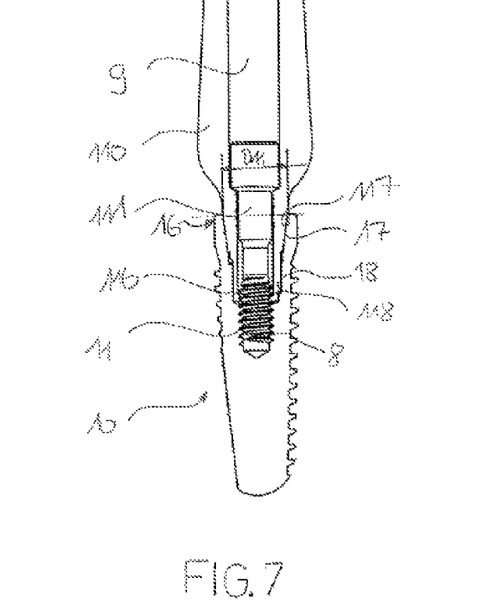
FIG. 7 shows a cross section through an abutment according to the invention and an implant according to the invention, along a central longitudinal plane.

FIG. 7 shows a cross section through an abutment 110, which is inserted into the implant 10 and is secured with an abutment screw 111 in the thread section 11 of the implant 10. The indexing sections 18, 118 of implant 10 and abutment 110 are in engagement with each other, such that rotation securing is produced. Because of the narrow tolerance of the surface 19, 119, the abutment 110 is guided in the implant 10 and thereby held precisely at its cervical end 116. The cone surface 117 of the abutment 110 and the cone surface 17 of the implant 10 are toleranced such that in any case contact between the cone surfaces 17, 117 is made in the area of the coronal end 16 of the implant. In this way, the abutment 110 can be supported in the implant 10 in two areas that are spaced apart axially from each other as far as possible. The support areas are at a maximal spacing, resulting in a particularly high degree of stability. At the same time, a gap between the abutment 110 and the implant 10 in the area of the coronal end 16 is avoided.

Figure 8:
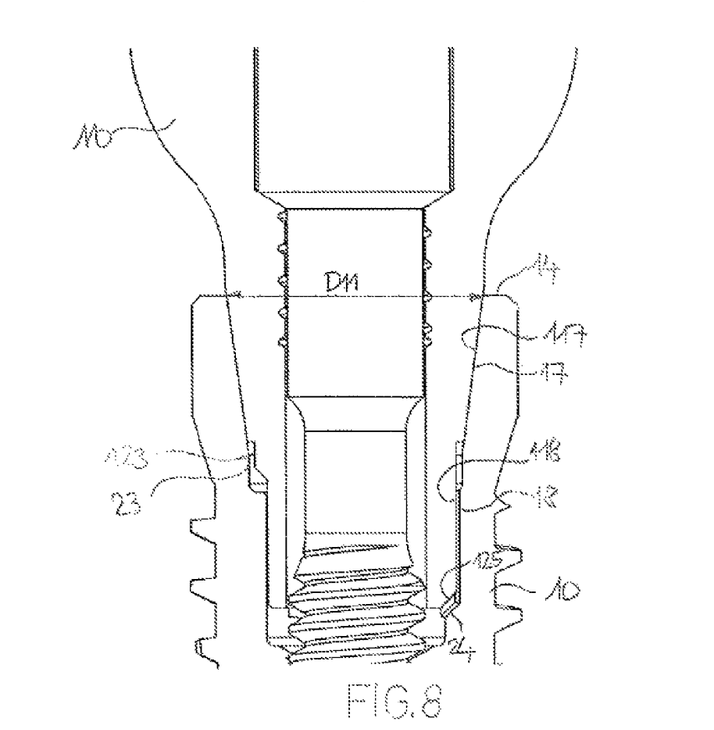
FIG. 8 shows an enlarged view of an abutment according to the invention in an implant according to the invention, in cross section along a central longitudinal plane in a connection area.

In the area where the abutment 110 issues from the implant 10, the abutment has an external diameter D11, which corresponds substantially to the internal diameter of the receiving opening 15 of the implant at its coronal end 16 (see also FIG. 8). As FIG. 8 also shows, the front edge 14 of the implant 10 is not covered by the abutment 110.

Figure 9:
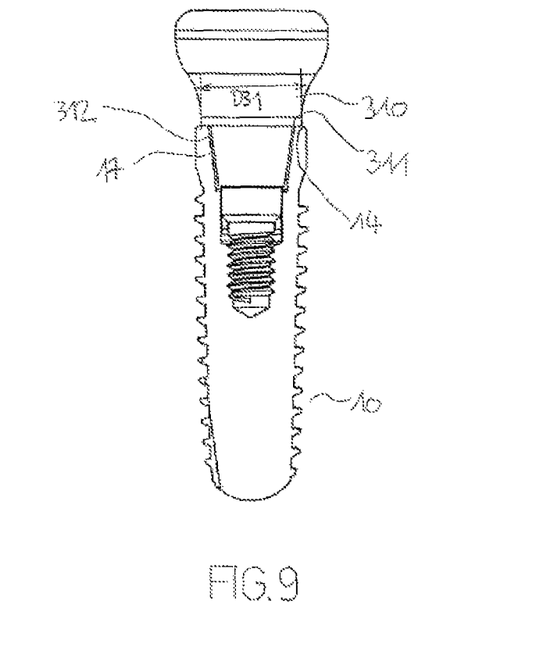
FIG. 9 shows a cross section through an implant according to the invention with a gingiva former, along a central longitudinal plane.

FIG. 9 shows the implant 10 from FIG. 1, into which implant an auxiliary element designed as a gingiva former 310 is inserted. Gingiva formers are known per se to a person skilled in the art. The gingiva former 310 is designed such that in the receiving opening 15 of the implant, and particularly in the cone section 17, there is no contact between the cone section 17 and the gingiva former 310. Instead, the gingiva former 310 rests with a contact face 311 on the front edge 14 of the implant 10. Damage to the cone surface 17 is avoided by means of the cone gap 312 between the cone surface 17 of the implant and the gingiva former. The external diameter D31 of the gingiva former in the area where it issues from the implant 10, i.e. adjacent to the front edge 14, is 3.5 mm. It is therefore greater than the 3.05 mm external diameter D11 of the abutment at the corresponding location (see FIGS. 7 and 8).

Figure 10:
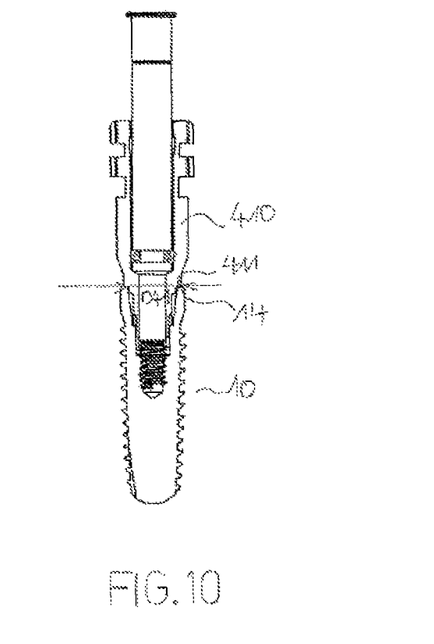
FIG. 10 shows a cross section through an implant according to the invention with an impression element, along a central longitudinal plane.
Figure 11:
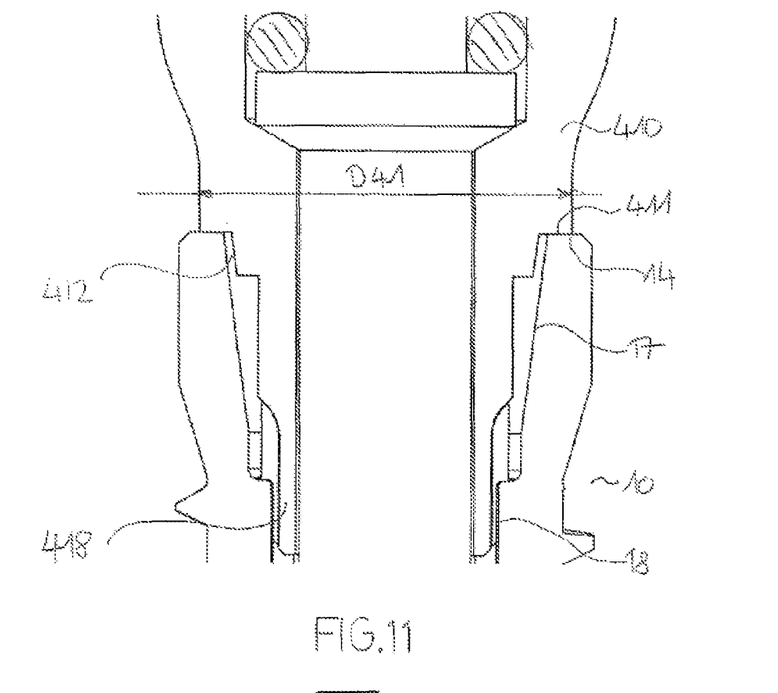
FIG. 11 shows an enlarged view of the impression element and of the implant from FIG. 10 in the area of the cone section of the implant.

FIGS. 10 and 11 show the implant 10 from FIG. 1, into which implant an auxiliary element designed as an impression element 410 is inserted.

The impression element 410 has a contact surface 411 which, in the inserted state, rests on the front edge 14 of the implant (see also FIG. 11). The impression element 410 is designed such that, in the inserted state, a cone gap 412 is formed between the impression element and the cone section 17 of the implant 10. In this way, the axial or vertical position of the impression element 410 with respect to the implant 10 is precisely defined by the contact between the contact surface 411 and the front edge 14. There is no vertical shift because of tolerances in the cone angles and the diameters.

The impression element 410 also has an indexing section 418 (not shown in detail), which is designed substantially the same as the indexing section 118 of the abutment (see FIGS. 4a, 4b).

The diameter D41 of the impression element in the area where it issues from the implant 10 is greater than the diameter D11 of the abutment at the same location (see FIGS. 7 and 8) and substantially the same as or slightly smaller than the external diameter D31 of the gingiva former at the corresponding location (see FIG. 9).

Figure 12:
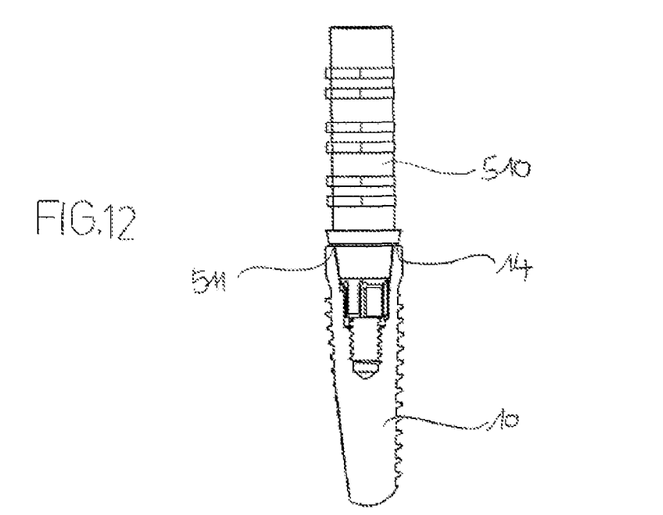
FIG. 12 shows a cross section through an implant according to the invention with a provisional abutment, along a central longitudinal plane.

Instead of the implant 10 and an abutment 110 as shown in FIG. 7, it is also possible to temporarily provide the implant 10 with a provisional abutment 510, which does not touch the cone surface of the implant 10 and which abuts against the front edge 14 of the implant 10 (see FIG. 12).

The implant 10 and the abutment 110 are produced and designed in a manner known per se. They are typically made of a biocompatible material such as titanium or ceramic. Depending on the tooth to be replaced, the implants and abutments have different dimensions, and therefore the measurements indicated above are to be considered as examples. For larger or smaller implants, the corresponding dimensions are uniformly reduced or increased, such that the relations between the individual lengths and diameters remain substantially unchanged.

The total cone angles always remain the same independently of the implant size, but the cone length can vary with different diameters.

By way of example, the individual measurements (in mm or mm$^2$) for implants with the diameters 3.3 mm, 3.8 mm (see also the above description), 4.3 mm and 5 mm are shown in the following table.

|  |  | Implant diameter | | | |
| --- | --- | --- | --- | --- | --- |
|  |  | ø 3.3 | ø 3.8 | ø 4.3 | ø 5 |
| Implant: |  |  |  |  |  |
| Cone angle (total) | α | 15° | 15° | 15° | 15° |
| Cone length | k | 1.5 | 1.9 | 1.9 | 1.9 |
| Cone diameter large |  | 2.8 | 3 | 3 | 3.8 |
| Cone diameter small |  | 2.4 | 2.5 | 2.5 | 3.3 |
| Length of cylindrical area | z | 0.6 | 0.4 | 0.4 | 0.4 |
| Indexing length | f | 1.9 | 1.8 | 1.8 | 1.8 |
| Guide surface between grooves | d2 | 2 | 2.1 | 2.1 | 2.7 |
| Groove length | n | 1.55 | 1.35 | 1.35 | 1.35 |
| Groove depth | t | 0.17 | 0.18 | 0.18 | 0.27 |
| Groove surface | 21 | 0.26 | 0.24 | 0.24 | 0.36 |
| Groove diameter | d1 | 2.35 | 2.45 | 2.45 | 3.25 |
| Abutment: |  |  |  |  |  |
| Cone angle (total) | β | 15° | 15° | 15° | 15° |
| Cone length | K | 1.6 | 1.9 | 1.9 | 1.9 |
| Cone diameter large |  | 2.85 | 3.05 | 3.05 | 3.85 |
| Cone diameter small |  | 2.42 | 2.56 | 2.56 | 3.36 |
| Cam length | N | 1.7 | 1.55 | 1.55 | 1.55 |
| Cam depth | T | 0.16 | 0.15 | 0.15 | 0.24 |
| Cam surface (without undercut) | 121 | 0.27 | 0.23 | 0.23 | 0.37 |
| External diameter of cam | D1 | 2.3 | 2.4 | 2.4 | 3.2 |
| Guide ø between cams | D2/121 | 2 | 2.1 | 2.1 | 2.7 |
| Cam width |  | 0.5 | 0.7 | 0.7 | 0.7 |
| Indexing length | F | 2.1 | 1.95 | 1.95 | 1.95 |
| Thread for disassembly tool |  | M1.8 | M1.8 | M1.8 | M2.3 |
| Diameter of gingiva former | D31 | 3 | 3.5 | 3.75 | 4.45 |
| Diameter of impression element | D41 | 3 | 3.5 | 3.75 | 4.45 |

The invention claimed is:

1. A dental implant for inserting into a jaw bone, said implant having a coronal end and a cervical end, and a receiving opening arranged at the coronal end of the implant, for receiving an abutment, wherein
the receiving opening, located adjacent the coronal end, has a cone section with a cone length and an indexing section with an indexing length, the cone section has an apex angle of 6° to 20°, and the cone section is located between the indexing section and the coronal end, wherein a cylindrical section, having a cylindrical section length, being arranged between the indexing section and the cone section,
the indexing length is at least 90% of the cone length, and
the indexing section is formed by a substantially cylindrical surface in which at least one groove, with a groove length, is arranged, the at least one groove extends radially outwards from the cylindrical surface and has a pair of radially extending opposed lateral groove surfaces which are at least partially planar and substantially parallel to one another,
the at least one groove can be brought into engagement with a cam of the abutment when the abutment is inserted into the implant,
said cylindrical surface is dimensioned and toleranced in such a way that said cylindrical surface forms a guide surface for said abutment,
the at least one groove has an external diameter which is less than or the same as a minimum diameter of the cone section, and
the groove length extends over at least 70% of the indexing length such that no further area serving to receive or guide the abutment is adjoined cervically to the indexing section.

2. The dental implant as claimed in claim 1, wherein the groove length extends substantially over the entire indexing length.

3. The dental implant as claimed in claim 1, wherein, seen in a cervical direction, the indexing section is adjoined directly by a threaded section for receiving an abutment screw.

4. The dental implant as claimed in claim 1, wherein the cylindrical surface of the indexing section has an external diameter which is greater than 80% of the external diameter of the at least one groove.

5. The dental implant as claimed in claim 1, wherein each surface of said pair of radially extending opposed lateral groove surfaces is greater than 0.22 mm$^2$.

6. The dental implant as claimed in claim 1, wherein the at least one groove has a groove depth, and the groove length is greater than 500% of the groove depth.

7. The dental implant as claimed in claim 1, wherein a circumferential platform surface is arranged between the cylindrical section and the indexing section, and the at least one groove extends in an axial direction as far as the platform surface.

8. The abutment as claimed in claim 1, wherein the cylindrical section and a platform are located between the cone section and the indexing section.

9. An abutment for a dental implant, said abutment having a coronal end and a cervical end, a surface at the coronal end for either directly or indirectly receiving a tooth replacement, and a connection area arranged at the cervical end for connection to the implant, wherein
the connection area has a cone section with a cone length, and an indexing section with an indexing length,
the cone section has an apex angle of 6° to 20°,
the indexing length is at least 70% of the cone length,
the cone section is located between the indexing section and the coronal end, wherein a cylindrical section, having a cylindrical section length, being arranged between the indexing section and the cone section, and
the indexing section is formed by a substantially cylindrical surface from which at least one cam with a cam length and a cam depth extends radially outwards, the at least one cam has a pair of substantially radially extending opposed lateral cam surfaces and the at least one cam can be brought into engagement with corresponding grooves of the implant, and the pair of substantially radially extending opposed lateral cam surfaces are at least partially planar and substantially parallel to one another,
said cylindrical surface is dimensioned and toleranced in such a way that said cylindrical surface forms a guide surface for a cylindrical surface of an indexing section of the implant when the abutment is inserted into the implant, and wherein
the at least one cam has an external diameter which is less than or the same as a minimum diameter of the cone section.

10. The abutment as claimed in claim 9, wherein the cam length extends over substantially the entire indexing length.

11. The abutment as claimed in claim 9, wherein the abutment has, adjacent in a cervical direction to the indexing section at the cervical end, a front face with an opening, through which a threaded section of an abutment screw can be guided.

12. The abutment as claimed in claim 9, wherein the cylindrical surface of the indexing section has an external diameter, which is greater than or equal to 80% of the external diameter of the at least one cam.

13. The abutment as claimed in claim 9, wherein each surface of said pair of radially extending cam surfaces is greater than 0.22 mm$^2$.

14. The abutment as claimed in claim 9, wherein the cam length is greater than 500% of the cam depth.

15. The abutment as claimed in claim 9, wherein the at least one cam has, at its cervical end, a chamfer.

16. The abutment as claimed in claim 9, wherein the cylindrical section and a platform are located between the cone section and the indexing section.

17. A combination of:
(a) an implant having a receiving opening which is arranged at a coronal end of the implant, wherein the receiving opening, seen from the coronal end, has a cone section with a cone length and an indexing section with an indexing length, the cone section having an apex angle of 6° to 20°, and the indexing length being at least 90% of the cone length, and the cone section is located between the indexing section and the coronal end, wherein a cylindrical section, having a cylindrical section length, being arranged between the indexing section and the cone section, and the indexing section is formed by a substantially cylindrical surface in which at least one groove with a groove length is arranged, wherein the at least one groove extends radially outwards from the cylindrical surface and has a pair of radially extending opposed lateral groove surfaces which are at least partially planar and parallel to one another,
the at least one groove has an external diameter which is less than or the same as a minimum diameter of the cone section, the groove length extends over at least 70% of the indexing length,
(b) an abutment having a surface for either directly or indirectly receiving a tooth replacement, and a connection area for connection to the implant, the connection area has a cone section with a cone length, and an indexing section with an indexing length, the cone section having an apex angle of 6° to 20°, and the indexing length being at least 70% of the cone length, and the indexing section is composed of a substantially cylindrical surface from which at least one cam with a cam length and a cam depth extends radially outward, the at least one cam has a pair of substantially radially extending opposed lateral cam surfaces which are at least partially planar and substantially parallel to one another, the at least one cam has an external diameter which is less than or the same as a minimum diameter of the cone section,
wherein the at least one groove of the implant corresponds to and can be brought into engagement with the at least one cam of the abutment, wherein the indexing sections and the cone sections of the implant and of the abutment are dimensioned and shaped in such a way that, when the abutment is inserted into the receiving opening of the implant, the cone sections at least partially touch each other and the indexing sections engage each other.

18. The combination as claimed in claim 17, wherein the cone sections of the implant and of the abutment are toleranced in such a way that, when the abutment is inserted into the receiving opening of the implant, contact between the cone sections takes place adjacent to a coronal front edge of the implant.

19. The combination as claimed in claim 17, wherein said cylindrical surface of the abutment's indexing section is dimensioned and toleranced in such a way that said cylindrical surface of the abutment's indexing section forms a guide surface for said cylindrical surface of the implant's indexing section, said cylindrical surface of the implant's indexing section being dimensioned and toleranced in such a way that said cylindrical surface of the implant's indexing section forms a guide surface for said cylindrical surface of the abutment's indexing section, and
the cylindrical surfaces of the indexing sections of the implant and abutment between the at least one cams of the abutment and between the at least one grooves of the implant are dimensioned such that the abutment is guided by the cylindrical surface of the implant's indexing section.

20. The combination as claimed in claim 17, comprising an abutment screw, wherein
the implant has a threaded section cervically adjacent its indexing section, for receiving the abutment screw,
the abutment has, cervically adjacent its indexing section at a cervical end of the abutment, a front face with an opening, through which a threaded section of the abutment screw can be guided.

* * * * *